US00PP21826P2

(12) United States Plant Patent
Dekker

(10) Patent No.: US PP21,826 P2
(45) Date of Patent: Mar. 29, 2011

(54) *CHRYSANTHEMUM* PLANT NAMED 'DEKCAVALLINI'

(50) Latin Name: *Chrysanthemum×morifolium*
Varietal Denomination: Dekcavallini

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/655,762

(22) Filed: Jan. 6, 2010

(51) Int. Cl.
*A01H 5/00* (2006.01)

(52) U.S. Cl. ..... Plt./288
(58) Field of Classification Search ..... Plt./288

See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Dekcavallini', characterized by its large decorative-type inflorescences with white-colored incurved ray florets; vigorous growth habit; strong and upright flowering stems; and excellent postproduction longevity.

2 Drawing Sheets

Botanical designation: *Chrysanthemum×morifolium.*
Cultivar denomination: 'DEKCAVALLINI'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dekcavallini'.

The new *Chrysanthemum* plant is a product of a planned breeding program conducted by the Inventor in Hensbroek, The Netherlands. The objective of the breeding program is to create new freely flowering decorative-type *Chrysanthemum* plants with attractive ray floret coloration and excellent postproduction longevity.

The new *Chrysanthemum* plant originated from a cross-pollination made by the Inventor in Hensbroek, The Netherlands on Oct. 1, 2004 of a proprietary selection of *Chrysanthemum×morifolium* identified as code number 41237, not patented, as the female, or seed, parent with a proprietary selection of *Chrysanthemum×morifolium* identified as code number 03.7864.02, not patented. The new *Chrysanthemum* plant was discovered and selected by the Inventor as a single flowering plant from within the progeny of the stated cross-pollination in a controlled greenhouse environment in Hensbroek, The Netherlands on May 5, 2005.

Asexual reproduction of the new *Chrysanthemum* plant by terminal cuttings in a controlled greenhouse environment in Hensbroek, The Netherlands since May 25, 2005, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekcavallini'.

These characteristics in combination distinguish 'Dekcavallini' as a new and distinct cultivar of *Chrysanthemum:*

1. Large decorative-type inflorescences with white-colored incurved ray florets.
2. Vigorous growth habit.
3. Strong and upright flowering stems.
4. Excellent postproduction longevity; plants maintain good substance for about four weeks in an interior environment.

Plants of the new *Chrysanthemum* differ from plants of the female parent selection in the following characteristics:

1. Plants of the new *Chrysanthemum* are more vigorous than plants of the female parent selection.
2. Plants of the new *Chrysanthemum* flower three days earlier than plants of the female parent selection.
3. Plants of the new *Chrysanthemum* have larger inflorescences than plants of the female parent selection.

Plants of the new *Chrysanthemum* differ from plants of the male parent selection in the following characteristics:

1. Plants of the new *Chrysanthemum* flower three days later than plants of the male parent selection.
2. Plants of the new *Chrysanthemum* have larger inflorescences than plants of the male parent selection.
3. Plants of the new *Chrysanthemum* and the male parent selection differ in ray floret color as plants of the male parent selection have yellow-colored ray florets.

Plants of the new *Chrysanthemum* can be compared to plants of *Chrysanthemum×morifolium* 'Anastasia', disclosed in U.S. Plant Pat. No. 13,550. In side-by-side comparisons conducted in Hensbroek, The Netherlands, plants of the new *Chrysanthemum* differed from plants of 'Anastasia' in the following characteristics:

1. Plants of the new *Chrysanthemum* were more vigorous than plants of 'Anastasia'.
2. Plants of the new *Chrysanthemum* had larger leaves than plants of 'Anastasia'.
3. Plants of the new *Chrysanthemum* had smaller inflorescences than plants of 'Anastasia'.
4. Ray florets of plants of the new *Chrysanthemum* were incurved whereas ray florets of plants of 'Anastasia' were straight.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dekcavallini' grown as a disbud type.

The photograph on the second sheet comprises close-up views of the upper (top of photograph) and lower surfaces (bottom of photograph) of typical inflorescences and leaves of 'Dekcavallini'.

DETAILED BOTANICAL DESCRIPTION

The aforementioned photographs and following observations and measurements describe plants grown during the autumn in Hensbroek, The Netherlands, under commercial practice in a glass-covered greenhouse. Plants were initially given nine days of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were nine weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Dekcavallini'.

Parentage:

*Female, or seed, parent.*—Proprietary selection of *Chrysanthemum×morifolium* identified as code number 41237, not patented.

*Male, or pollen, parent.*—Proprietary selection of *Chrysanthemum×morifolium* identified as code number 03.7864.02, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous decorative-type cut flower that is typically grown as a disbud-type; vigorous growth habit.

*Flowering stem description (peduncles).*—Aspect: Erect. Strength: Strong. Length: About 80 cm to 90 cm. Stem diameter: About 7 mm. Internode length: About 1 cm to 3 cm. Texture: Finely pubescent; longitudinally ridged. Color: Close to 146A to 146B.

*Foliage description.*—Arrangement: Alternate; simple. Length: About 8 cm to 12 cm. Width: About 4.5 cm to 7.5 cm. Apex: Acute. Base: Attenuate. Margin: Palmately and crenately lobed; sinuses convergent. Texture, upper and lower surfaces: Pubescent, rough; veins prominent on lower surface. Venation pattern: Pinnate, reticulate. Color: Developing leaves, upper surface: Close to 137A. Developing leaves, lower surface: Close to 147B. Fully developed leaves, upper surface: Close to 147A; venation, close to 147B. Fully developed leaves, lower surface: Close to 147B; venation, close to 147C. Petiole: Length: About 1.5 cm to 3 cm. Diameter: About 3.5 mm. Texture, upper and lower surfaces: Rough. Color, upper surface: Close to 146A to 146B. Color, lower surface: Close to 146B to 146C.

Inflorescence description:

*Appearance.*—Decorative-type inflorescence form with oblong to quilled-shaped incurved ray florets; inflorescences borne on terminals, arising from leaf axils; ray and disc florets develop acropetally on a capitulum.

*Fragrance.*—Moderately fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); early and uniform flowering response; plants exposed to nine days of long day/short night conditions after planting followed by photoinductive short day/long night conditions flower about 52 days later when grown as a disbud-type.

*Postproduction longevity.*—In an interior environment, inflorescences and foliage will maintain good color and substance for about four weeks; inflorescences persistent.

*Quantity of inflorescences.*—Grown as a disbud type only the terminal inflorescence is allowed to develop.

*Inflorescence size.*—Diameter: About 12 cm to 14 cm. Depth (height): About 3.5 cm. Disc diameter: About 3 mm, inconspicuous. Receptacle height: About 6 mm. Receptacle diameter: About 1.2 cm. Receptacle color: Close to 145C.

*Inflorescence buds.*—Shape: Flattened spherical to rounded. Height: About 6 mm. Diameter: About 8 mm. Color: Close to 137C.

*Ray florets.*—Length: About 3.5 cm to 6.5 cm. Width: About 5 mm to 10 mm. Shape: Oblong or quilled; incurved. Apex: Emarginate. Base: Fused. Margin: Entire. Texture, upper and lower surfaces: Smooth, glabrous; satiny. Number per inflorescence: About 250 arranged in numerous whorls. Color: When opening, upper and lower surfaces: Close to NN155D; towards the base, close to 150B. Fully opened, upper and lower surfaces: Close to NN155D; towards the base, close to 150B.

*Disc florets.*—Shape: Fused tubular, elongated. Apex: Dentate. Length: About 7 mm. Diameter: About 1 mm. Number per inflorescence: About 25, massed at the center of the receptacle. Color: Apex: Close to 145A. Mid-section: Close to 13B. Base: Close to 155B.

*Involucral bracts.*—Length: About 1 cm to 1.4 cm. Width: About 3 mm to 8 mm. Shape: Ovate. Apex:

Rounded. Base: Truncate. Margin: Entire. Texture, upper surface: Smooth, glabrous. Texture, lower surface: Pubescent; slightly rough. Number per inflorescence: About 50 arranged in about three to four whorls. Color, upper surface: Close to 137C. Color, lower surface: Close to 137A.

*Reproductive organs.*—Androecium: Not observed. Gynoecium: Present on both ray and disc florets. Style length: About 5 mm. Style color: Yellow. Stigma color: Yellow.

*Seed/fruit.*—Seed and fruit production have not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekcavallini' as illustrated and described.

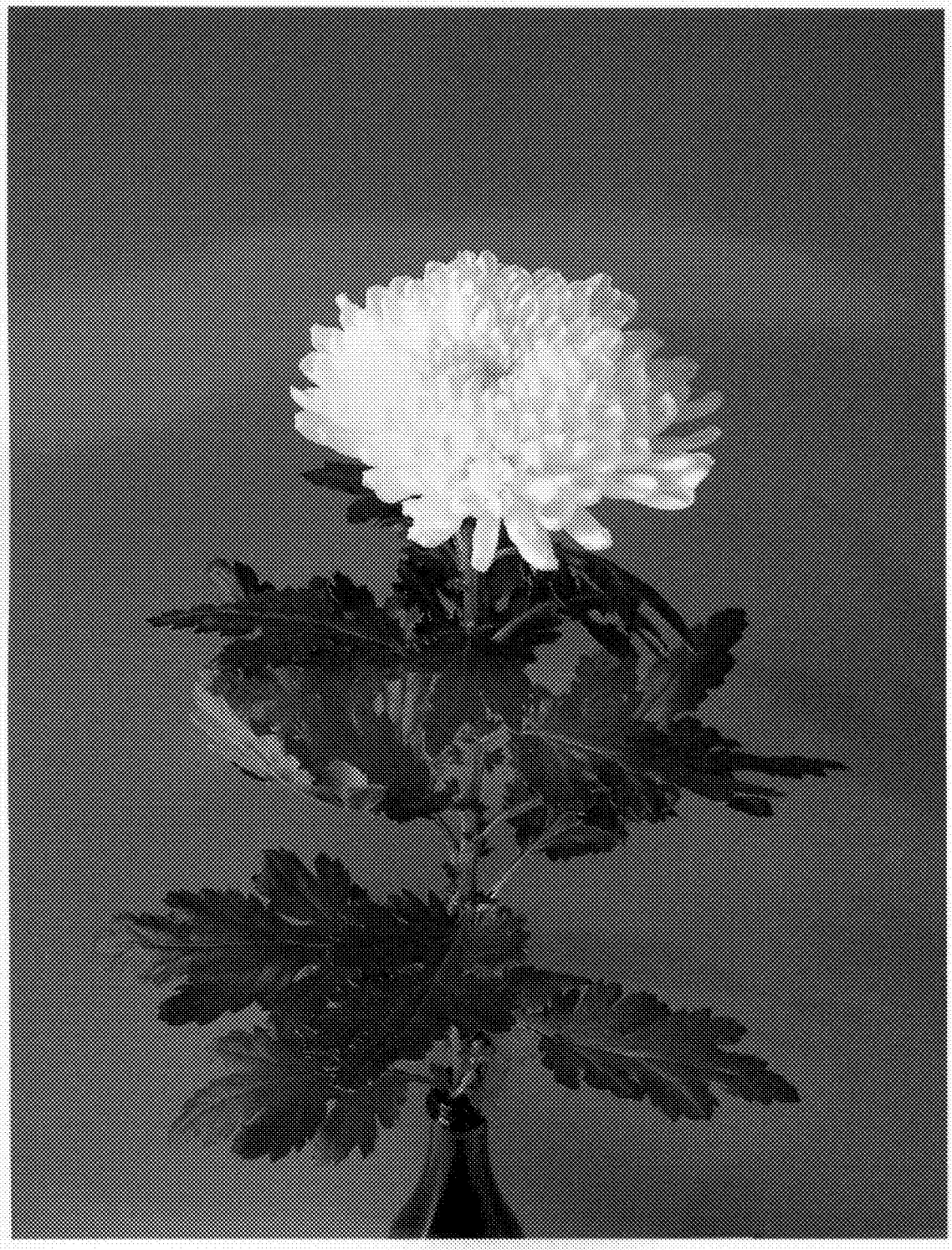

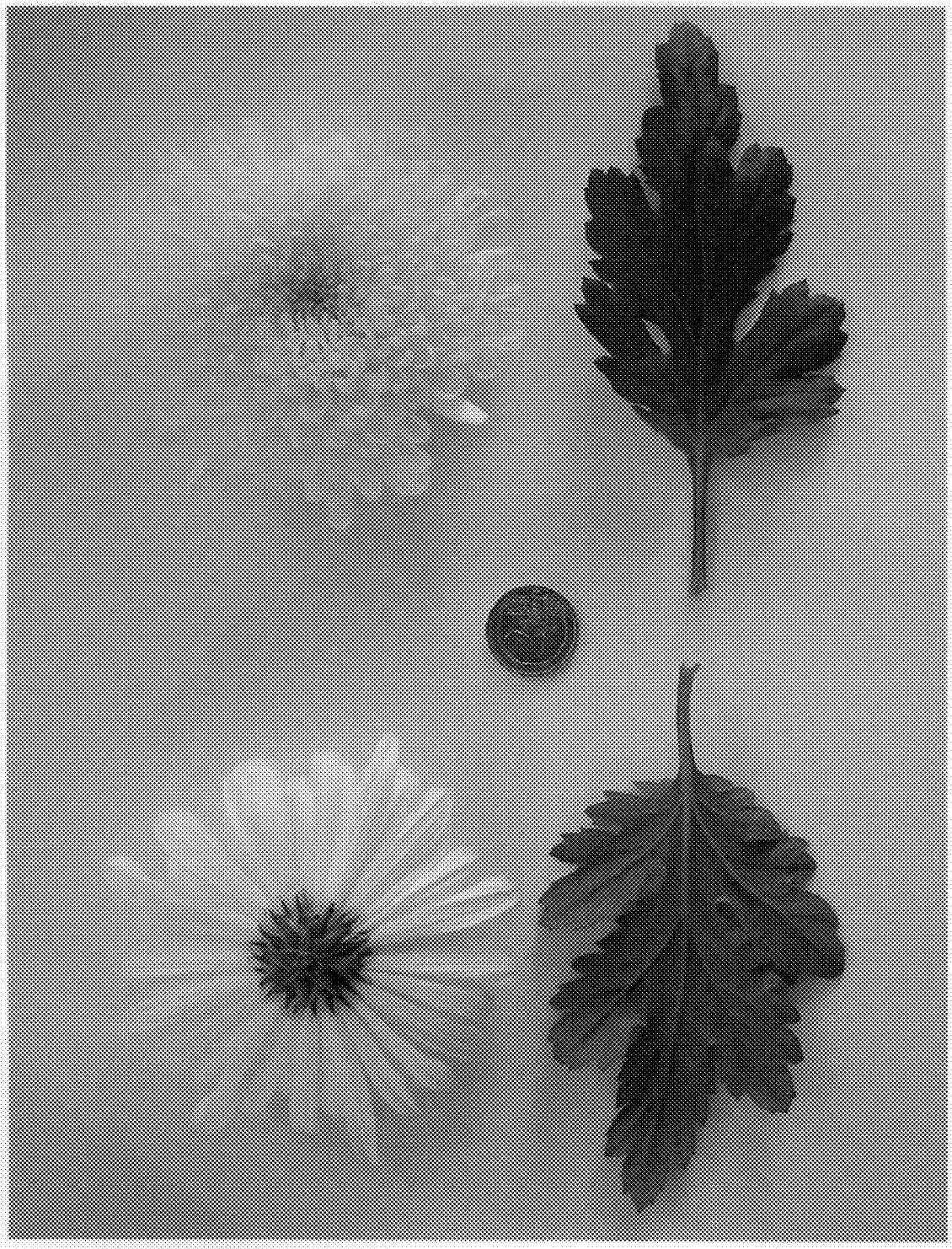

* * * * *